United States Patent [19]

Jaxa-Chamiec et al.

[11] Patent Number: 5,110,875
[45] Date of Patent: May 5, 1992

[54] POLYSTYRENE ANION EXCHANGE POLYMERS

[75] Inventors: Albert A. Jaxa-Chamiec, Rickmansworth; Deirdre M. B. Hickey, Welwyn, both of England

[73] Assignee: Smith Kline & Franch Laboratories Limited, Welwyn Garden City, England

[21] Appl. No.: 536,837

[22] Filed: Jun. 12, 1990

[30] Foreign Application Priority Data

Jun. 14, 1989 [GB] United Kingdom ............... 8913699

[51] Int. Cl.$^5$ ............................................. C08F 8/32
[52] U.S. Cl. .............................. 525/332.2; 521/32; 525/379; 525/380; 525/382
[58] Field of Search .................. 525/332.2; 521/32

[56] References Cited

U.S. PATENT DOCUMENTS

| | | |
|---|---|---|
| 3,989,088 | 8/1975 | Cohen et al. |
| 4,198,395 | 4/1980 | De Simone |
| 4,273,898 | 6/1981 | Amick ........................... 521/32 |
| 4,311,799 | 1/1982 | Miyake et al. ................. 521/32 |
| 4,373,031 | 2/1983 | Waite ............................ 521/32 |
| 4,510,128 | 4/1985 | Khanna |
| 4,532,128 | 7/1985 | Sheldon et al. |
| 4,721,666 | 1/1988 | Yamanouchi et al. |

FOREIGN PATENT DOCUMENTS

| | | |
|---|---|---|
| 929391 | 6/1963 | United Kingdom |
| 1286949 | 12/1969 | United Kingdom |
| 2026501-A | 2/1980 | United Kingdom |

OTHER PUBLICATIONS

Walfish, et al., Water, Air & Soil Pollution 12:477-484.
Carpov, et al., J. Macromol. Sci. Chem., A22(5-7):907-929 (1985).
Takeuchi, et al., Chem. Pharm. Bull. 32(3):823-831 (1984).
Petrariu, et al., Revue Roumaine de Chimie, 25:145-154 (1980).
Wessling, et al., Makromol. Chem., suppl. 10/11:319-333 (1985).

Primary Examiner—Bernard Lipman
Attorney, Agent, or Firm—Wayne J. Dustman; Stuart R. Suter; Edward T. Lentz

[57] ABSTRACT

Polymers bearing a quaternary ammonium group are disclosed as being useful in lowering serum cholesterol levels in man. A compound of the invention is N-(2-N,N-dimethylamino)ethyl)-N,N-dimethylammoniomethyl-substituted polystyrene, chloride salt.

11 Claims, No Drawings

POLYSTYRENE ANION EXCHANGE POLYMERS

The present invention relates to novel polystyrene anion exchange resins, pharmaceutical compositions containing them and their use in the lowering of plasma cholesterol levels in humans.

Coronary Heart Disease (CHD) is one of the most serious health problems of contemporary society. Worldwide epidemiological studies have shown that the incidence of CHD is related to a number of independent risk factors, in particular, for example, high concentrations of serum cholesterol (hypercholesterolaemia). Such adverse factors lead to atherosclerosis, and ultimately, in severe cases, intermittent claudication, cerebrovascular insufficiency, thrombosis and cardiac arrest.

It is known that ion exchange resins, in particular polystyrene resins can be used as sequestering agents to bind non-absorbed bile acids and salts in the intestinal tract, forming complexes which are then excreted in the faeces. This sequestering leads to a decrease in the amount of bile acids returning to the liver via enterohepatic circulation. The synthesis of replacement bile acids from hepatic cholesterol depletes hepatic cholesterol, regulates hepatic LDL receptors and consequently reduces plasma cholesterol levels. Such sequestering resins have been recognized as useful for the treatment of hypercholesterolaemia. In addition, it is now proven that reducing serum cholesterol with bile acid sequestrants has a beneficial effect on protecting against the occurrence of atherosclerosis.

One particular agent which is currently used to lower serum cholesterol levels in humans by binding bile acids in the intestinal tract is cholestyramine. Cholestyramine is a cross-linked anion exchange polystyrene resin bearing an ionisable trimethylammonium group bound to the polymer backbone. However, the use of this agent is associated with a number of undesirable side-effects, for example, it is unpalatable and must be taken in high doses and causes, in some cases, flatulence and other gut side-effects. In addition, its ability to bind bile acids lacks specificity and is inefficient with respect to the amounts of resin which it is necessary to use. Other polystyrene resins are known in the art, in particular GB 2204586-A discloses a series of resins bearing a bisammonium group. However, such compounds are disclosed as antibacterial agents with no indication that they have cholesterol lowering properties.

It is the object of the present invention to provide compounds which overcome the disadvantages of this known sequestering agent and provide improved bile acid sequestering agents which are useful for lowering serum cholesterol levels in humans.

The present invention therefore provides in a first aspect, polymers of structure (I):

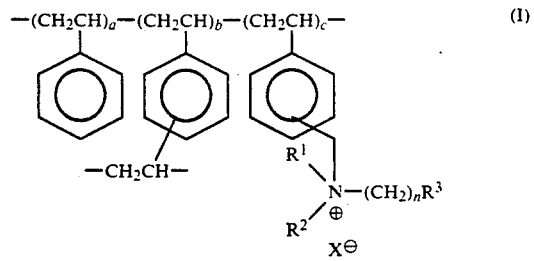

in which, $R^1$ and $R^2$ are each $C_{1-4}$alkyl, or one is $C_{1-4}$alkyl and the other is $-(CH_2)_nR^3$;

n is 2 to 12;

$R^3$ is $NR^4R^5$ or $N^{\oplus}R^6R^7R^8 X^{\ominus}$;

$R^4$ and $R^5$ are the same or different and are each hydrogen, $C_{1-4}$alkyl, $C(=NH)NH_2$, or together with the nitrogen atom to which they are attached form a saturated or unsaturated ring optionally containing one or more further heteroatoms.

$R^6$, $R^7$ and $R^8$ are the same or different and are each hydrogen, $C_{1-4}$alkyl or one of $R^6$, $R^7$ and $R^8$ is $C_{1-4}$alkyl and the other two together with the nitrogen atom to which they are attached form a saturated or unsaturated ring optionally containing one or more further heteroatoms;

a, b and c are numbers which indicate the relative molar percentages of the units present in said polymer, (b) being from 1 to 10 molar percent, and (c) being from 30 to 98 molar percent; and $X^{\ominus}$ is a counter ion.

Suitably the groups $R^1$ and $R^2$ are $C_{1-4}$alkyl or one of $R^1$ and $R^2$ is $C_{1-4}$alkyl and the other is $(CH_2)_nR^3$; preferably $R^1$ and $R^2$ are both $C_{1-4}$alkyl; most preferably $R^1$ and $R^2$ are both methyl.

Suitably $R^3$ is $NR^4R^5$ or $N^{\oplus}R^6R^7R^8X^{\ominus}$;

Suitably, $R^4$ and $R^5$ are the same or different and are each hydrogen, $C_{1-4}$alkyl, $C(=NH)NH_2$ or together form a ring.

More suitably, one of $R^4$ and $R^5$ is hydrogen or $C_{1-4}$alkyl and the other is hydrogen, $C_{1-4}$alkyl or $C(=NH)NH_2$.

Preferably, one of $R^4$ and $R^5$ is hydrogen or $C_{1-4}$ alkyl and the other is hydrogen, $C_{1-4}$ alkyl or $C(=NH)NH_2$; most preferably $R^4$ and $R^5$ are the same and are each hydrogen or $C_{1-4}$alkyl.

Suitably, $R^6$, $R^7$ and $R^8$ are the same or different and are each hydrogen or $C_{1-4}$alkyl or together form a ring; more suitably $R^6$, $R^7$ and $R^8$ are all the same. Preferably $R^6$, $R^7$ and $R^8$ are all $C_{1-4}$alkyl, most preferably, methyl.

Suitable saturated or unsaturated rings $R^4$ and $R^5$ are formed by two of $R^6$ to $R^8$ will be apparent to those skilled in the art, but include, in particular rings of structure

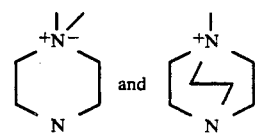

Suitably (b) is from 1 to 10 molar percent of said polymer, preferably (b) is from 2 to 5 molar percent of said polymer.

Suitably $X^{\ominus}$ is a counter ion as hereinafter defined; more suitably $X^{\ominus}$ is a chloride, sulphate or phosphate ion, preferably $X^{\ominus}$ is a chloride ion.

Other examples of suitable counter ions $X^{\ominus}$ will be apparent to those skilled in the art and include, in particular, physiologically acceptable counter ions such as halides, in particular chloride, sulphates or phosphates, bicarbonates, carbonates, formates, acetates, sulphonates, propionates, malonates, succinates, malates, tartrates, citrates, maleates, fumarates, ascorbates, glucuronates or the anions of amino acids such as aspartic or glutamic acid.

The polystyrene resins of the present invention are also characterized by their total exchange capacity i.e. the theoretical maximum capacity of the resin if each counter ion were to be exchanged with bile acid. In this specification the total exchange capacity is defined in terms of the number of milliequivalents of counter ion per gram of dry weight of polymer.

Suitable total exchange capacities are in the range of, for example where the counter ion $X^-$ is chlorine, from 1.5 to 10 meq $Cl^-$ per gram of resin. Preferred within this range are resins having a total exchange capacity of between 2 and 6 meq $Cl^-$/gram of resin.

It is to be noted that the term 'bile acid' when used herein shall be taken to include bile acids, bile salts and conjugates thereof The polystyrene resins of the present invention can be prepared by processes analogous to those known in the art. For example by:

(a) reaction of a polymer of structure (II)

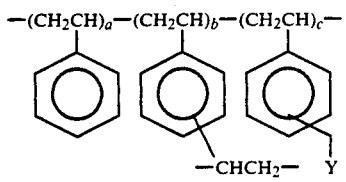

(II)

in which a, b and c are as described for structure (I) and Y is a group displaceable by an amine, with an amine of structure $R^1R^2N(CH_2)_nR^3$ (II) in which $R^1$ to $R^3$ and n are as described for structure (I); or (b) reaction of a polymer of structure (IV)

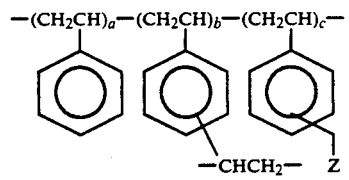

(IV)

in which a, b and c are as described for structure (I) and Z is $NR^1R^2$ or $NR^1(CH_2)_nR^3$ in which $R^1$ to $R^3$ and n are as described for structure (I), with a compound of structure $R^4Y$ (V) in which $R^4$ is $(CH_2)_nR^3$ when Z is $NR^1R^2$ or a group $R^2$ when Z is $NR^1(CH_2)_nR^3$, and Y is a group displaceable by an amine.

The reaction between a polymer of structure (II) and a compound of structure (III) can be carried out in a suitable solvent at elevated temperature. Suitable solvents included for example, a $C_{1-4}$alkanol, dimethylformamide or N-methylpyrrolidone. Preferably the reaction is carried out in dimethylformamide at a temperature of between about 60° and 80° for a period of up to 24 hours or until the reaction is complete.

The reaction between a polymer of structure (IV) and a compound of structure (V) can be carried out in a suitable inert solvent such as a $C_{1-4}$alkanol, dimethylformamide or N-methylpyrrolidone at elevated temperature.

The intermediate polymers of structure (II) are available commercially or can be prepared from readily available materials by methods known to those skilled in the art. For example polymers of structure (II) in which Y is chlorine can be prepared by reaction of chloromethylstyrene, styrene and divinyl benzene in an aqueous suspension comprising polyvinyl alcohol in the presence of an initiator at elevated temperature. Suitable initiators will be apparent to those skilled in the art and include, in particular azobisisobutyronitrile.

The intermediate polymers of structure (IV) can be prepared from the polymers of structure (II) by reaction with an amine of structure $HNR^1R^2$ or $HNR^1(CH_2)_nR^3$ in which $R^1$ to $R^3$ and n are as described for Structure (I) under the same or similar conditions as indicated for the reaction of a compound of structure (II) and a compound of structure (III). Alternatively the intermediate polymers of structure (IV) can be prepared by polymerization of appropriate monomer mixtures under standard polymerization conditions.

The intermediate polymers of structure (II) can be prepared directly from polystyrene by methods analogous to those known in the art, for example where $Y^-$ is chloride by chloromethylation of polystyrene.

The polystyrene resins of structure (I) have been found to bind bile acids both in in vitro and in in vivo models in that they increase the amount of bile acids in the faeces. As indicated earlier it is well recognized that removal of bile acids from the intestinal tract in this way lowers serum cholesterol levels and also has a beneficial effect on protecting against atherosclerosis and its dependent clinical conditions. The present invention therefore provides in a further aspect, the use of polystyrene resins of structure (I) in therapy, in particular for the lowering of serum cholesterol levels in mammals, including humans. In addition the polymers of structure (I) are expected to be of use in protecting against atherosclerosis and its sequelae.

In view of the foregoing the present invention also provides a method of lowering serum cholesterol levels in mammals which comprises administering to a mammal in need thereof an effective serum cholesterol lowering amount of a compound of structure (I); and a method of protecting against atherosclerosis.

When used in therapy in the methods of the invention, the polystyrene resins of structure (I) are in general administered in a pharmaceutical composition.

In a still further aspect of the present invention there is therefore provided a pharmaceutical composition comprising a polystyrene resin of structure (I) in association with a pharmaceutically acceptable carrier.

The compositions of the present invention can be prepared by techniques well known to those skilled in the art of pharmacy and include all those known for the formulation of polystyrene resins for human use.

The polymers are preferably administered as formulations in admixture with one or more conventional pharmaceutical excipients which are physically and chemically compatible with the polymer, which are non-toxic, are without deleterious side-effects but which confer appropriate properties on the dosage form.

In general, for liquid formulations aqueous pharmaceutically acceptable carriers such as water or aqueous dilute ethanol, propylene glycol, polyethylene glycol or glycerol or sorbitol solutions are preferred. Such formulations can also include flavoring and sweetening agents such as sucrose, fructose, inert sugar, cocoa, citric acid, ascorbic acid, fruit juices etc. In general, digestible oil or fat based carriers should be avoided or minimized as they contribute to the condition sought to be alleviated by use of the polymers. They are also subject to absorption by the polymers during prolonged contact, thus reducing the capacity of the polymer to absorb dietary fats after administration.

The polymers can also be prepared as concentrates, for dilution prior to administration, and as formulations suitable for direct oral administration. They can be administered orally ad libitum, on a relatively continuous basis for example by dispersing the polymer in drinks or food.

Preferably, the polymers are administered in tablet form or in gelatin capsules containing solid particulate polymer or an aqueous or semi-aqueous suspension of solid polymer containing a suitable suspending agent.

Preferably the polymer is administered in unit dosage form, each dosage unit containing preferably from 0.5 g to 1 g of polymer.

The daily dosage regimen for an adult patient may be, for example, an oral dose of between 1 and 10 g, preferably 1-5 g the compound being administered 1 to 4 times a day. Suitably the compound is administered for a period of continuous therapy of one month or more sufficient to achieve the required reduction in serum cholesterol levels.

In addition the polymers of the present invention can be co-administered (together or sequentially) with further active ingredients such as HMGCoA reductase inhibitors and other hypocholesterolaemic agents, and other drugs for the treatment of cardiovascular diseases.

The following data and examples indicate the properties and preparation of the polymers of the present invention. Temperatures are recorded in degrees centigrade. The exchange capacity of the ammonium substituted resins was determined by elemental analysis and/or potentiometric titration of chloride ion. Figures quoted are expressed as milli equivalents of exchangeable chloride ion per gram of dry resin weight.

EXAMPLE 1

A suspension of chloromethyl-substituted polystyrene (5.0 g, 4.09 meq Cl/g) in dimethylformamide (DMF) (50 ml) was treated with N,N,N'N,N'-tetramethylethylenediamine (23.76 g) and the mixture stirred at room temperature for 72 hours. The polymer was then filtered off and washed with methanol and diethyl ether and dried in vacuo to give N-(2-(N,N-dimethylamino)ethyl)-N,N-dimethylammoniomethylsubstituted polystyrene, chloride salt, as polymer beads (7.39 g) (2.77 meq Cl$^-$/g, 5.09 meq N/g) (Example 1).

EXAMPLE 2

To a suspension of N-(2-(N,N-dimethylamino)ethyl)-N,N-dimethylammoniomethyl-substituted polystyrene (Example 1) (1.0 g) in methanol (50 ml), iodomethane (0.68 g) was added and the mixture stirred at room temperature for 18 hours and at reflux temperature for 1 hour. The polymer was filtered off and washed with aqueous 1 N hydrochloric acid, water, methanol and diethyl ether and dried to give N,N-dimethyl-N-(2-(N,N,N-trimethylammonio)ethyl)-ammoniomethyl-substituted polystyrene, dichloride salt, as polymer beads (0.89 g) (4.45 meq Cl$^-$/g, 4.31 meq N/g) (Example 2).

EXAMPLE 3

The substituted polymer prepared in Example 1 (1.0 g) was treated with 1-iodobutane (6.2 g) in methanol (50 ml) at reflux temperature for 72 hours. The polymer was filtered off and washed and dried as in Example 2 to give N,N-dimethyl-N-(2-(N,N-dimethyl-N-butylammonio)ethyl) ammoniomethyl-substituted polystyrene, dichloride salt, as polymer beads (0.92 g) (3.65 meq Cl$^-$/g, 3.91 meq N/g) (Example 3).

EXAMPLE 4

A solution of N,N-dimethylethylenediamine (6.56 g) and S-methyl-thiuronium sulphate (10.36 g) in ethanol (200 ml) was heated at reflux temperature for 18 hours. The solvent was evaporated to give N-(2-guanidinoethyl)-N,N-dimethylamine.

This material was re-dissolved in ethanol (200 ml), added to a suspension of chloromethyl-substituted polystyrene (5.0 g) (3.72 meq Cl/g) in DMF (100 ml), and this mixture heated at 60° for 18 hours. The polymer was filtered off and washed with aqueous 2 N hydrochloric acid, methanol, water, methanol and diethyl ether and dried to give N-(2-guanidinoethyl)-N,N-dimethylammoniomethyl-substituted polystyrene, chloride salt, hydrochloride, as polymer beads (8.35 g) (3.94 meq Cl$^-$/g, 8.04 meq N/g) (Example 4)

EXAMPLE 5

(a) A suspension of chloromethyl-substituted polystyrene (5.0 g) (3.72 meq Cl/g) in DMF (50 ml) was treated with N,N-dimethyl-N-(3-trifluoroacetamidopropyl)amine (18.5 g) and the mixture heated at 60° for 18 hours. The polymer was filtered off and washed with methanol and diethyl ether and dried at 90° in vacuo of 18 hours to give N,N-dimethyl-N-(3-trifluoroacetamidopropyl)ammoniomethyl-substituted polystyrene, chloride salt, as polymer beads (9.36 g) (2.10 meq Cl$^-$/g, 4.17 meq N/g).

(b) A suspension of the above polymer (8.0 g) in ethanol (50 ml) was treated with aqueous 4 N sodium hydroxide solution (100 ml) and the mixture heated at reflux temperature for 18 hours. The polymer was filtered off and washed with water, methanol, diethyl ether methanolic/aqueous hydrochloric acid, water, ethanol and diethyl ether to give N-(3-ammoniopropyl)-N,N-dimethylammoniomethyl-substituted polystyrene, dichloride salt, as polymer beads (5.07 g) (4.23 meq Cl$^-$/g, 4.35 meq N/g) (Example 5).

EXAMPLE 6

The bis-ammonium-substituted plystyrene prepared in Example 5b (3.65 g) was suspended in methanol (50 ml) and treated with iodomethane (12.8 g) and anhydrous sodium carbonate (12.0 g). The resulting mixture was heated at 50° for 18 hours. The polymer was filtered off and washed with water, methanol and diethyl ether and dried to give (3-(N,N,N-trimethylammonio)propyl)-N,N-dimethylammoniomethyl-substituted polystyrene, dichloride salt, as polymer beads (4.17 g) (3.60 meq Cl$^-$/g, 3.55 meq N/g) (Example 6).

EXAMPLE 7

(a) A suspension of chloromethyl-substituted polystyrene (10.0 g) (3.72 meq Cl/g) in DMF (100 ml) was treated with a solution of dimethylamine in ethanol (200 ml of 33% solution) at room temperature for 6 days. The polymer was filtered off and washed with ethanol and diethyl ether to give N,N-dimethylaminomethyl-substituted polystyrene as white beads (10.4 g) (3.50 meq N/g).

(b) A suspension of the above polymer (2.85 g) in DMF (30 ml) was treated with N-(6-bromohex-1-yl)-phthalimide (6.25 g) at 80° for 20 hours. The polymer was filtered off and washed with methanol and diethyl ether to give N-(6-(1-phthalimido)hex-1-yl)-N,N-dimethyl-ammoniomethyl-substituted polystyrene, chloride salt, (5.8 g).

(c) The above phthalimido-substituted polymer (5.8 g) was suspended in ethanol (500 ml) and treated with hydrazine hydrate (2.0 g). The mixture was heated at reflux temperature for 18 hours, aqueous 2 N sodium hydroxide added and the polymer filtered off. The polymer was washed with water, aqueous 2 N hydrochloric acid solution, water, methanol and diethyl ether and dried to give N-(6-ammoniohex-1-yl)-N,N-dimethylammoniomethyl-substituted polystyrene, dichloride salt, as white polymer beads (4.27 g) (3.99 meq Cl$^-$/g, 3.94 meq N/g) (Example 7).

EXAMPLE 8

A suspension of the above bis-ammonium-substituted polymer (Example 7c) (2.37 g) in methanol (50 ml) was treated with iodomethane (6.6 g) and anhydrous sodium carbonate (5.3 g) in a method analogous to that described for Example 6 to give after work-up N-(6-(N,N,N-trimethylammonio)hex-1-yl)-N,N-dimethylammoniomethyl-substituted polystyrene, dichloride salt, as white polymer beads (2.10 g) (3.80 meq Cl$^-$/g, 3.63 meq N/g).

EXAMPLE 9

(a) Anhydrous sodium carbonate (149 g) was added to a solution of N,N-bis(3-aminoprop-1-yl)-N-methylamine (50.5 g) in diethyl ether (500 ml) and the mixture cooled to 0°. Trifluoroacetic anhydride (150 g) was added dropwise and the mixture stirred at room temperature for 18 hours, water added and the aqueous solution extracted with diethyl ether. The diethyl ether extracts were washed with aqueous saturated sodium chloride solution, dried and evaporated to give N,N-bis(3-trifluoroacetamidoprop-1-yl)-N-methylamine as a colorless oil (69.3 g).

(b) A suspension of chloromethyl-substituted polystyrene (5.0 g) (3.72 meq Cl/g) in DMF (50 ml) was treated with a N,N-bis(3-trifluoroacetamido-prop-1-yl)-N-methylamine (11.4 g) at 60° for 18 hours. After work-up as described for Example 6, the corresponding quaternary ammonium-substituted polymer was isolated (11.45 g). A suspension of the above polymer (9.8 g) in ethanol (100 ml) was treated with aqueous 4 N sodium hydroxide solution (200 ml) at reflux temperature for 18 hours. The polymer was filtered off and washed with water, aqueous 2 N hydrochloric acid solution, water, methanol and diethyl ether and dried to give N,N-bis(3-ammonioprop-1-yl)-N-methylammoniomethyl-substituted polystyrene, trichloride salt, (8.2 g) (4.85 meq Cl$^-$/g, 4.93 meq N/g) (Example 9)

EXAMPLE 10

A suspension of the tris-ammonium-substituted polymer described in Example 9b (7.0 g) in methanol (200 ml) was treated with iodomethane (28.6 g) and anhydrous sodium carbonate (21.3 g) by a method analogous to that described in Example 6, to give, after work-up, N,N-bis(3-(trimethyl- ammonio)prop-1-yl)-N-methylammoniomethyl-substituted polystyrene, trichloride salt, as white polymer beads (7.6 g) (3.88 meq Cl$^-$/g, 4.27 meq N/g) (Example 10).

EXAMPLE 11

A solution of N,N-dimethyl-N-(11-hydroxyundecyl)amine (1.1 g), triphenylphosphine (1.34 g) and phthalimide (0.75 g) in dry THF (20 ml) was treated with diethylazodicarboxylate (0.94 g, 95%). The resultant mixture was stirred for 18 hours, evaporated to dryness and the residue triturated with ether. The precipitated crystals were removed by filtration. The filtrate was evaporated to dryness and the residue was chromatographed on silica gel, eluted with chloroform and then chloroform:methanol:methanolic ammonia (89:10:1), to give N,N-dimethyl-N-(11-phthim;idoundecyl)amine (0.75 g) as a brown, low melting solid.

This amine (13.01 g) was mixed with chloromethylated polystyrene (5.1 g, 3.72 meq Cl/g) in DMF (50 ml) and stirred at 60° for 12 hours. After work up as described in Example 1, N,N-dimethyl-N-(11-phthamidoundecyl)ammonio-methyl-substituted polystyrene, chloride salt was obtained as a cream colored resin (11.70 g).

This polymer (2.02 g) was added to a solution of hydrazine hydrate (2.02 g) in ethanol (65 ml) and the mixture heated at reflux temperature for 6 hours. The polymer was filtered off, washed with potassium hydroxide solution (1%, 50 ml), ethanol and hydrochloric acid in ethanol (10%, 250 ml). The polymer was returned to the reaction flask with a hydrazine hydrate (0.53 g) and ethanol (50 ml) and the mixture heated for a further 1 hour. The polymer was again filtered off and the washing repeated. The polymer was then further washed with methanol and ether, and dried at 60° (0.5 mmHg) for 24 hours to give N,N-dimethylN-(11-ammonioundec-1-yl)-ammoniomethyl-substituted polystyrene, dichloride salt, as white polymer beads (1.60 g) (3.88 meq Cl$^-$/g).

EXAMPLE 12

1% cross-linked chloromethyl-substituted polystyrene (4.0 g, 4.09 meq Cl/g) was treated with 1,4-diazabicyclo[2.2.2]octane (18.3 g) in DMF (80 ml) at 45° for 1 hour and at 65° for 5 hours. The polymer was filtered off and washed with DMF, methanol and diethyl ether to give (4-aza-1-azoniobicyclo[2.2.2]oct-1-yl)-methyl-substituted polystyrene, chloride salt, as white polymer beads (6.1 g, 2.97 meq Cl$^-$/g).

EXAMPLE 13

A suspension of 1% cross-linked chloromethyl-substituted polystyrene (5.0 g, 4.09 meq Cl/g) in DMF (40 ml) was treated with N,N,-dimethylpiperazine (22.35 g) at 75° for 5 hours then allowed to stand at room temperature for 56 hours. The polymer was filtered off and washed with DMF, methanol, and diethyl ether and dried to give N'-methyl-N-methylpiperaziniomethyl-substituted polystyrene, chloride salt, as white polymer beads (7.08 g, 2.52 meq Cl$^-$/g, 5.08 meq N/g).

EXAMPLE 14

A suspension of N,-methyl-N-methylpiperaziniomethyl-substituted polystyrene, chloride salt, (1.75 g) (2.52 meq Cl$^-$/g, 5.08 meq N/g) in methanol (30 ml) was treated with iodomethane (1 ml) and the mixture stirred at 30° for 3 hours. Iodomethane (1 ml) was added and the mixture stirred at room temperature for 24 hours. The polymer was filtered off and washed with methanol, methanol/diethyl ether, diethyl ether, aqueous/methanolic hydrochloric acid, give N',N'-dimethyl-N-methyl-piperaziniomethyl-substituted polystyrene, dichloride salt, as off-white polymer beads (1.44 g, 4.44 meq Cl$^-$/g, 4.60 meq N/g).

DATA

Bile Acid Binding assay

Test compound (150 mg) was equilibrated with 5 mM sodium glycocholate (30 ml)—a typical physiological concentration—in Krebs, buffer for 3 hours. The compound was separated by centrifugation and the total bound determined by subtraction of the amount in the supernatant from the total bile acid used. Bile acid dissociation was measured by resuspending the compound in Kreb's, buffer, shaking and sampling the mixture through a filter at several time points up to 20 minutes. Radioactivity and hence bile acid dissociated was determined in the filtrate (Table I).

TABLE I

| Example No. | GC Bound mmoles/g | | % Dissociated |
|---|---|---|---|
| | t = 0 | t = 2 minutes | |
| 3 | 0.72 | 0.62 | 14 |
| 4 | 0.83 | 0.72 | 13 |
| 5 | 0.72 | 0.61 | 15 |
| 6 | 0.74 | 0.58 | 22 |
| 7 | 0.78 | 0.65 | 17 |
| 8 | 0.64 | 0.51 | 20 |
| 9 | 0.74 | 0.59 | 20 |
| 10 | 0.67 | 0.50 | 22 |
| Cholestyramine | 0.75 | 0.50 | 33 |

What is claimed is:

1. A pharmaceutical composition comprising a polymer of structure

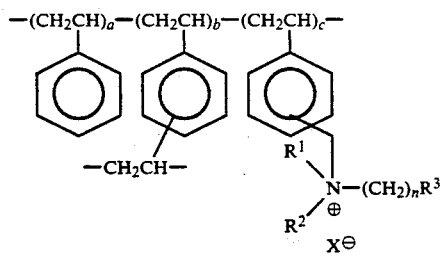

(I)

in which,

R1 and R$^2$ are each C$_{1-4}$alkyl, or one is C$_{1-4}$alkyl and the other is —(CH$_2$)$_n$R$^3$;

n is 2 to 12;

R$^3$ is NR$^4$R$^5$ or N$^\oplus$R$^6$R$^7$R$^8$ X$^\ominus$;

R$^4$ and R$^5$ are the same or different and are each hydrogen, C$_{1-4}$alkyl, C(=NH)NH$_2$, or together with the nitrogen atom to which they are attached form a saturated or unsaturated ring optionally containing one or more further heteroatoms.

R$^6$, R$^7$ and R$^8$ are the same or different and are each hydrogen, C$_{1-4}$alkyl or one of R$^6$, R$^7$ and R$^8$ is C$_{1-4}$alkyl and the other two together with the nitrogen atom to which they are attached form a saturated or unsaturated ring optionally containing one or more further heteroatoms;

a, b and c are numbers which indicate the relative molar percentages of the units present in said polymer, (b) being from 1 to 10 molar percent, and (c) being from 30 to 98 molar percent; and X$^\ominus$ is a counter ion.

2. A pharmaceutical composition according to claim 1 in which R$^1$ and R$^2$ both C$_{1-4}$ alkyl.

3. A pharmaceutical composition according to claim 2 in which (b) is from 2 to 5 molar percent of said polymer.

4. A pharmaceutical composition according to claim 1 wherein the polymer is a N,N-dimethyl-N-(2-(N,N-dimethyl-N-butylammonio)ethyl-substituted polystyrene derivative.

5. A pharmaceutical composition according to claim 1 wherein the polymer is a N-(2-guanidinoethyl)-N,N-dimehthlammonio)ethyl-substituted polystyrene derivative.

6. A pharmaceutical composition according to claim 1 wherein the polymer is a N-(3-(ammoniopropyl)-N,N-dimethylammoniomethyl-substituted polystyrene derivative.

7. A pharmaceutical composition according to claim 1 wherein the polymer is a (3-(N,N,N-trimethylammonio)propyl-N,N-dimethylammoniomethyl-substituted polystyrene derivative.

8. A pharmaceutical composition according to claim 1 wherein the polymer is a N-(6-ammoniohex-1-yl)-N,N-dimethylammonioethyl-substituted polystyrene derivative.

9. A pharmaceutical composition according to claim 1 wherein the polymer is a N-(6-(N,N,N-trimethylammonio)hex-1-yl)-N,N-dimethylammoniomethyl-substituted polystyrene derivative.

10. A pharmaceutical composition according to claim 1 wherein the polymer is a N,N-bis-(3-ammonioprop-1-yl)-N-methylammoniomethyl-substituted polystyrene derivative.

11. A pharmaceutical composition according to claim 1 wherein the polymer is a N,N-bis-(3-trimethylammonio)prop-1-yl)-N-methylammoniomethyl-substituted polystyrene derivative.

* * * * *